United States Patent [19]

Klaveness et al.

[11] Patent Number: 5,718,884
[45] Date of Patent: Feb. 17, 1998

[54] MICROBUBBLE-BASED CONTRAST AGENTS WITH CROSSLINKED AND REDUCED PROTEINACEOUS SHELLS

[75] Inventors: Jo Klaveness, Oslo; Pal Rongved, Nesoddtangen; John Henrik Johansen, Oslo; Per Antonius Foss, Oslo; Anders Høgset, Oslo; Anne Marie Hvoslef, Sørumsand, all of Norway

[73] Assignee: Nycomed Imaging AS, Oslo, Norway

[21] Appl. No.: 397,065

[22] PCT Filed: Sep. 3, 1993

[86] PCT No.: PCT/GB93/01861

§ 371 Date: May 4, 1995

§ 102(e) Date: May 4, 1995

[87] PCT Pub. No.: WO94/06477

PCT Pub. Date: Mar. 31, 1994

[30] Foreign Application Priority Data

| Sep. 16, 1992 | [GB] | United Kingdom | 9219595 |
| Sep. 30, 1992 | [GB] | United Kingdom | 9220638 |
| Sep. 30, 1992 | [GB] | United Kingdom | 9220639 |

[51] Int. Cl.$^6$ .................................................. A61K 49/04
[52] U.S. Cl. .................................................. 424/9.52
[58] Field of Search .................... 424/9.52, 9.51, 424/9.321, 489, 450; 128/662.02

[56] References Cited

U.S. PATENT DOCUMENTS

| 4,452,773 | 6/1984 | Molday | 424/1.1 |
| 5,284,646 | 2/1994 | Menz et al. | 424/9 |
| 5,501,863 | 3/1996 | Rössling et al. | 424/489 |

FOREIGN PATENT DOCUMENTS

| 0 224 934 | 6/1987 | European Pat. Off. |
| 0 441 468 | 8/1991 | European Pat. Off. |
| 92 05806 | 4/1992 | WIPO |

OTHER PUBLICATIONS

Oestensen et al., *Chemical Abstracts*, vol. 116, No. 23, 8 Jun. 1992, abstract No. 231235m.

*Primary Examiner*—Gary E. Hollinden
*Assistant Examiner*—Michael G. Hartley
*Attorney, Agent, or Firm*—Bacon & Thomas

[57] ABSTRACT

The present invention pertains to proteinaceous gas- or gas precursor-containing microbubble contrast agents for use in ultrasound and/or MR imaging, in which the protein matrix is crosslinked by reaction with a bifunctional aldehyde (e.g., a dialdehyde such as glutaraldehyde or an α,β-unsaturated aldehyde such as acrolein) in an aqueous medium at substantially neutral pH. The contrast agents exhibit improved in vivo and storage stabilities, particularly if the matrix is also reacted with a Schiff's base reducing agent such as a borohydride. Modification of the size distribution of such crosslinked proteinaceous gas-containing contrast agents, e.g. to reduce the mean size of the microbubbles, further enhances their stability and permits preparation of novel contrast agents having a particularly narrow microbubble size distribution.

23 Claims, No Drawings

MICROBUBBLE-BASED CONTRAST AGENTS WITH CROSSLINKED AND REDUCED PROTEINACEOUS SHELLS

This invention relates to novel contrast agents, more particularly to new gas-containing or gas-generating contrast agents of use in diagnostic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems as ultrasound contrast agents.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars.

It will be appreciated that for applications in echocardiography such bubble systems should preferably not exceed 8–10 microns in diameter in order to permit free passage through the capillary beds of the pulmonary system to the left atrium and ventricular cavity, with a view to facilitating ultrasonic visualisation of the left side of the heart and myocardium following intravenous injection of the contrast agent. To provide effective visualisation of the left side of the heart such bubble systems (which will hereinafter be referred to as "microbubbles") will clearly be required to exhibit adequate stability in vivo, preferably for more than one passage of circulation.

It will likewise be apparent that preformed microbubble contrast agent systems desirably exhibit good storage stability, for example in order to permit manufacture at a central location and distribution to and storage at hospitals etc. prior to use.

One area which has attracted a substantial volume of research is the manufacture of protein-encapsulated gas microbubbles for use as ultrasound contrast agents. As described in U.S. Pat. No. 4,718,433 and U.S. Pat. No. 4,774,958 such agents may, for example, be prepared by sonicating a viscous protein solution to generate a microbubble system and thermally or chemically denaturing at least a part of the encapsulating protein to stabilise the microbubbles. Thermal denaturation may be effected by application of heat or simply by heat generated during sonication. Chemical denaturation is effected by reaction of the protein with formaldehyde or glutaraldehyde, e.g. in an aqueous medium at pH 4.5. A preferred proteinaceous starting material is 5% human serum albumin (HSA); its use is said to encourage the formation of small microbubbles primarily having a diameter in the range 2–4 microns. Microspheres produced by this technique are said to be stable on storage for 48 hours or longer.

EP-A-0324938 describes a process for preparing an improved protein-encapsulated microbubble system of the above type. This process involves a two stage sonication procedure in which the sonicator horn is first immersed in the protein solution to generate a microbubble system and is then withdrawn to a position above but proximate to the surface of the solution to induce foaming and aerosolating thereof. This is said to produce a concentrated dispersion of microbubbles predominantly of diameters less than 10 microns, which dispersion is said to be stable for 4–8 weeks or longer on storage at ambient temperature, e.g. 20°–25° C. A continuous process intended to be suitable for commercial production of such protein-encapsulated microspheres is described in EP-A-0359246.

HSA is again a preferred protein for the above procedures and may be used in solution at concentrations of, for example, 0.5–25% w/w, the use of commercially available 5% aqueous solutions or diluted versions thereof, e.g. to a concentration of 0.5–3.% w/w, being convenient. HSA is used in this way to prepare the experimental product Albunex®, which comprises microspheres having air microbubble centres and insolubilised (i.e. denatured) HSA walls.

While such products exhibit a reasonable level of in vitro stability during storage, as described in the above-mentioned EP-A-0324938 and EP-A-0359246, their stability in vivo following administration to a test subject has been found to be capable of improvement. Thus, for example, Shapiro et al. in J. Am. Coll. Cardiol. 16(7) (1990), pp. 1603–1607 have reported lack of reproducible and quantifiable myocardial opacification following intravenous injection of sonicated HSA ultrasound contrast agents in humans. These workers also observed a rapid decrease in left ventricular contrast intensity at the left ventricular base and apex in early systole, associated with almost total disappearance of contrast by end-systole, and suggest that this is probably due to destruction of the albumin-coated microbubbles by high left ventricular systolic pressure.

A similar observation is contained in EP-A-92/05806, where it is stated that the comparative rigidity of the encapsulating membranes in products according to EP-A-0324938 may lead to their rupture in the blood stream through pressure variations due to heart pulsations. This document suggests that potential ultrasound membranes may be prepared by foaming an aqueous solution of a filmogenic protein and reducing the foam bubbles to a desired size range (e.g. 0.5–10 microns, preferably 4–10 microns) by application of shear (e.g. by attrition or by sonic or ultrasonic vibration). The product may be stabilised by thermal denaturation or by reaction with a protein-reactive crosslinking agent, e.g. an aldehyde or a sulphide such as cysteine, the use of aqueous formaldehyde and aqueous glutaraldehyde being illustrated. The resulting products do not appear, however, to exhibit consistently long term storage stability unless they are freeze-dried for subsequent reconstitution with water or other physiologically acceptable liquid for injection—it will be appreciated that there are significant practical advantages in avoiding this need for reformulation prior to use.

There is thus an ongoing need for contrast agents comprising protein-encapsulated gas microbubbles or gas-generating systems which exhibit improved in vivo stability combined with good storage stability.

The present invention is based inter alia on our finding that the stability of protein-based contrast agents may be substantially enhanced if the protein is reacted with a bifunctional aldehyde capable of effecting crosslinking of the protein, said reaction being effected in an aqueous medium at substantially neutral pH. More particularly we have surprisingly found that the level of stability enhancement obtainable in this way may significantly exceed that obtained using acidic aqueous formaldehyde or glutaraldehyde in accordance with prior art such as the above-mentioned U.S. Pat. No. 4,718,433 and U.S. Pat. No. 4,774,958, especially if the crosslinking reaction is carried out in an aqueous medium which is buffered to substantially neutral pH.

The term "substantially neutral pH" as used herein refers to the central pH region which is not markedly either acidic or basic, for example the pH range 5–9.

Thus according to one aspect of the present invention we provide contrast agents comprising microbubbles of gas or a gas precursor encapsulated in a shell of protein crosslinked by reaction in an aqueous medium at substantially neutral pH with a bifunctional aldehyde capable of effecting crosslinking of the protein.

The protein component can be any protein or derivative thereof, including polyamino acids. Albumin, gelatin and γ-globulin are representative compounds, the use of human serum albumin being preferred. Such proteins may be obtained from biological sources, for example from human or animal blood, or produced by a lower organism using recombinant technology. A typical method for preparation of human serum albumin by fermentation is described in WO 90/02808.

The encapsulating protein is advantageously at least partially denatured, e.g. as a result of thermal treatment (which may for example be directly induced by sonication), as well as being crosslinked in accordance with the invention. The contrast agents of the invention may thus conveniently be obtained by crosslinking preformed sonicated protein-based contrast agents, for example sonicated albumin products such as Albunex®.

Bifunctional aldehydes which may be used to stabilise the ultrasound contrast agents of the invention include dialdehydes and α,β-unsaturated aldehydes. Representative dialdehydes include aliphatic dialdehydes, e.g. containing up to 10 carbon atoms, such as glutaraldehyde, adipaldehyde and 1,8-octanedial, and substituted derivatives thereof, such as 2-hydroxy-adipaldehyde. Representative α,β-unsaturated aldehydes include α,β-unsaturated aliphatic aldehydes containing up to 10 carbon atoms, for example $C_{3-8}$ 2-alkenals such as acrolein (i.e. 2-propenal), methacrolein (i.e. 2-methyl-2-propenal), crotonaldehyde (i.e. 2-butenal), 2-pentenal and 2-hexenal, and substituted derivatives thereof such as 3-dimethylaminoacrolein.

In accordance with an additional embodiment of the invention the contrast agents may advantageously be further stabilised by reaction with a reducing agent serving to reduce the double bond of a Schiff's base (e.g. a borohydride reagent such as sodium borohydride or sodium cyanoborohydride) as described in greater detail hereinafter.

According to a further aspect of the invention we provide a process for the preparation of a microbubble contrast agent which comprises crosskinking a protein by reaction in an aqueous medium at substantially neutral pH with a bifunctional aldehyde capable of effecting crosslinking of the protein, a gas or a gas precursor being encapsulated in said protein before, during or after said crosslinking reaction.

Any biocompatible gas may be employed in this process and in the contrast agents of the invention, for example air, nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The gas may be free within the microbubble or may be trapped or entrained within a containing substance. The term "gas" as used herein includes any substance in gaseous form at 37° C.

Gas precursors include carbonates and bicarbonates, e.g. sodium or ammonium bicarbonate and aminomalonate esters.

For ultrasonic applications such as echocardiography, in order to permit free passage through the pulmonary system and to achieve resonance with the preferred imaging frequency of about 0.1–15 MHz, it may be convenient to prepare and use microbubbles having an average size of 0.1–10 µm, e.g. 1–7 µm. Substantially larger bubbles, e.g. with average sizes of up to 500 µm, may however be useful in other applications, for example gastrointestinal imaging or investigations of the uterus or Fallopian tubes.

Generation of the microbubble system may be effected by any convenient means, e.g. by any of the appropriate methods described in the prior art. Thus, for example, gas may be entrapped in a protein solution simply by vigorously shaking the solution in the presence of the gas, i.e. creating a gas-in-liquid emulsion, for example as described in U.S. Pat. No. 4,684,479. Another well known method comprises passing the gas through a syringe into a solution of the protein. As described in U.S. Pat. No. 3,900,420 a microgas emulsion may be created by using an apparatus for introducing gas rapidly into a fast-flowing liquid; a region of low pressure is thereby created in the liquid, which in this instance will be a protein solution, into which the gas is introduced and the gas-in-liquid system so obtained is pumped from the apparatus.

By using electrolysis it is possible to generate a gas to be entrapped directly in a container containing a protein solution. The electrolyte or electrolytes necessary for electrolysis may additionally help to stabilize the protein-encapsulated microbubbles. An aqueous solution containing one or more electrolytes will typically generate hydrogen gas at the cathode and oxygen at the anode; on adding hydrazine, nitrogen gas may be generated at the anode. The electrodes may be separated by a salt bridge. Using the Kolbe reaction, one may also generate $CO_2$ from carboxylic acids using electrolysis.

A preferred method of generating the gas microbubble system comprises sonication of a protein solution in the presence of (e.g. under an atmosphere of) the gas to be encapsulated, for example as described in the above-mentioned U.S. Pat. No. 4,718,433, U.S. Pat. No. 4,774,958, EP-A-0324938 or EP-A-0359246. One advantage of such sonication techniques is that they may be operated so as to effect a controlled degree of denaturation of the encapsulating protein in addition to the required microbubble generation, thereby enhancing the stability of the final product.

Crosslinking of the protein in accordance with the invention is conveniently effected using a solution or suspension of the protein in water or, more preferably, in an aqueous buffer system. The aldehyde may be employed in pure liquid form or in solution in water or a water-miscible cosolvent, e.g. a lower alkanol such as ethanol, for example to give a 50% solution; the amount of aldehyde used is conveniently about 2–50 equivalents relative to the protein.

The crosslinking reaction may, for example, be effected at room temperature or with heating, although it may be undesirable for the reaction temperature to exceed about 60°

C. since this may promote unwanted and excessive denaturation of the protein. The reaction medium is advantageously subjected to very gentle agitation, for example in a rotating flask. Reaction times will typically be in the range 1 minute–24 hours.

The crosslinking reaction may, for example, be carried out at a pH of 5 –9, preferably at a pH of 6–8 such as pH 7. Where the reaction is effected in aqueous buffer, any appropriate buffer system may in general be used, e.g. as is conventional in the art. Thus, for example, a citrate/sodium hydroxide system may be used to provide a pH of about 5 or 6, phosphate buffered saline may be used to provide a pH of about 7, a borate/hydrochloric acid system may be used to provide a pH of about 8, and a borate/potassium chloride/ sodium hydroxide system may be used to provide a pH of about 9.

While we do not wish to be bound by theoretical considerations, it is believed that where an α,β-unsaturated aldehyde is employed the crosslinking reaction involves, inter alia, a rapid Michael-type addition of primary amine groups in the protein to the β-carbon atom of the α,β-double bond and a slower reaction between the aldehyde function and further protein primary amine groups leading to formation of e.g. a Schiff's base containing —CH=N— linkages and/or products containing —CH(OH)—NH— linkages (see, for example, the findings of Sebenik et al. in Polymer 31 (1990), pp. 130–134). Crosslinking using dialdehydes is believed to proceed predominantly through formation of such —CH=N— and —CH(OH)—NH— linkages.

As indicated above, the crosslinked protein may advantageously additionally be reacted with a reducing agent serving to reduce the double bond of a Schiff's base, such as sodium borohydride or sodium cyanoborohydride; such reducing agents are conveniently employed in an amount of 2–5 equivalents relative to the aldehyde used for crosslinking. This reaction is conveniently effected at an optionally buffered pH of 5–9, preferably pH 6–8 such as pH 7, and may, if desired, be carried out simultaneously with the crosslinking reaction; thus the reducing agent may be added to the protein solution or suspension before the aldehyde is added.

The crosslinking reaction and any reduction reaction are preferably effected on proteinaceous material in which a gas or a gas precursor has already been encapsulated, particularly on such materials which have undergone preliminary stabilisation as a result of controlled denaturation of the encapsulating protein. Useful protein starting materials for the crosslinking reactions thus include preformed sonicated protein-based ultrasound contrast agents, for example sonicated albumin products such as Albunex®.

Such preformed protein materials, hereinafter referred to as "microspheres", are desirably washed prior to crosslinking to remove free non-encapsulating protein which would otherwise unnecessarily participate in the crosslinking reaction. This may be effected by, for example, water-washing the microspheres 3 or 4 times, allowing the microspheres to float after each washing step and withdrawing the underlying wash water, e.g. using a pipette. A suspension of the microspheres, e.g. in water or a suitable buffer system may then be subjected to reaction with the aldehyde and, if desired, a reducing agent, e.g. in a rotating flask, and thereafter washed, e.g. with water, to remove unreacted aldehyde and any reducing agent.

The product of the crosslinking reaction may possess aldehyde groups at the surfaces of the microbubbles (see e.g. Pharmaceutical Research 9(6) (1992), p. 776 and J. Pharm. Sci. 7(12) (1982), p. 1323). Such aldehyde groups will be converted to hydroxymethyl groups when the crosslinked product is subjected to a reduction reaction. Alternatively they may be reacted with an amine, preferably used in large excess, leading to formation of a Schiff's base, which may if desired thereafter be treated with a reducing agent serving to reduce the —CH=N— double bonds thereof, e.g. as hereinbefore described. Use of a bifunctional amine permits replacement of the aldehyde grouping by a functional group of choice; thus, for example, reaction with an amino acid will lead to introduction of carboxyl groups, reaction with an amino alcohol will lead to introduction of hydroxyl groups and reaction with a diamine will lead to introduction of amino groups.

We have additionally found that both the in vitro and in vivo stabilities of gas-containing contrast agents according to the invention may be further enhanced if the microbubbles are subjected to size distribution modification as well as to crosslinking and to any chemical reduction reaction, the term "size reduction" being used herein to denote a reduction in the mean size of the microbubbles. Such size distribution modification may, for example, involve a reduction in the mean size of the microbubbles and/or a narrowing of the size range for the microbubbles, and may be effected before, during or, more preferably, after the crosslinking and any chemical reduction reaction. Contrast agents comprising such size distribution modified microbubbles constitute a further feature of the invention.

One size distribution modification technique which may be employed comprises application of an external pressure of gas (e.g. air or oxygen) to the microbubbles or, more preferably, to a suspension thereof, e.g. in water or buffer such as phosphate buffered saline. Thus, for example, a suspension of gas-filled microbubbles may be treated with gas at a pressure of e.g. 20–100 kPa, advantageously 30–80 kPa, preferably 60–70 kPa; the treatment may conveniently be effected at room temperature in a pressure vessel, e.g. for 30 seconds–5 minutes, advantageously for about 1 minute.

Alternatively, gas-filled microbubbles may be size distribution modified by treatment with a liquid in which the gas content is soluble, e.g. water or buffer such as phosphate buffered saline in the case of air-filled microbubbles, for example by gently agitating the microbubbles in such a liquid, e.g. in a rotating flask. The extent of the size distribution modification is governed by both the volume of liquid employed relative to the gas volume of the microbubbles and the dissolved gas content of the liquid, increasing as the former increases and decreasing as the latter increases; these parameters may therefore be controlled to give a desired degree of size distribution modification.

Size distribution modification such that the mean volume of the microbubbles is reduced by 40–60%, e.g. by about 50%, has been found to give particularly enhanced stability, coupled with high levels of acoustic attenuation when the products are used as ultrasound contrast agents. Thus, for example, such size distribution modified contrast agents of the invention have been found to give strong enhancement of both arterial and venous Doppler signals in rabbits.

Size distribution modified contrast agents according to the invention are also characterised by high in vitro stability, e.g. showing no loss of contrast effect over 90 seconds in standard in vitro tests for ultrasound contrast effect.

Using such size distribution modification techniques it is possible to prepare crosslinked proteinaceous contrast agents in which a substantial majority, e.g. at least 85%, preferably at least 90%, of the microbubbles have sizes up to 4 μm, the remainder having sizes in the range 4–10 μm;

this may be compared with, for example, the contrast agent exemplified in U.S. Pat. No. 4,718,433, where approximately 20% of the microbubbles have sizes exceeding 4 µm. Crosslinked protein-encapsulated gas microbubble contrast agents having such a size distribution are novel products which are particularly useful in, for example, ultrasound techniques such as echocardiography and constitute a further feature of the invention. They may be prepared from crosslinked protein-based microbubble-containing contrast agents other than those stabilised by crosslinking with bifunctional aldehydes in accordance with the present invention, for example from biodegradably crosslinked protein-encapsulated microbubble contrast agents such as are described in WO 92/17213.

In general the number and size distribution of products prepared in accordance with the invention may be determined by e.g. Coulter counter analysis. With this information standardised suspensions of microspheres containing a predetermined total volume of gas per unit volume of suspension may be formulated.

The contrast agents of the invention may be used in a variety of diagnostic imaging techniques, including ultrasound, MR and X-ray imaging. Their use in diagnostic ultrasonic imaging and in MR imaging, e.g. as susceptibility contrast agents, constitute preferred features of the invention.

The following non-limitative examples serve to illustrate the invention. All temperatures are in °C. The number concentrations of the microspheres in the Albunex® suspensions used as starting materials were generally in the range $5–9\times10^8$/ml.

EXAMPLE 1

50% Ethanolic acrolein (30 µl) was added to a suspension of water-washed Albunex® microspheres (3 ml) in sterile water in a glass vial, and the vial was gently rolled on a standard roller mixer for 4 hours.

The resulting microsphere suspension was characterised by Coulter counter measurements; the relative gas volume of the microspheres was calculated and the suspension was standardised by adjusting its volume to a value where the gas volume was identical to that of a reference suspension of untreated Albunex® microspheres prior to echogenicity measurements being made.

EXAMPLES 2–6

The procedure of Example 1 was repeated except that acrolein was replaced by the aldehydes listed in the following Table:

| Example | Reagent µl | Gas Vol. % | Reagent (50% in ethanol) |
| --- | --- | --- | --- |
| 1 | 30 | 89 | Acrolein |
| 2 | 30 | 85 | Crotonaldehyde |
| 3 | 30 | 13 | 2-Hexenal |
| 4 | 30 | 71 | Glutaraldehyde* |
| 5 | 15 | 33 | 2-Hydroxyadipaldehyde* |
| 6 | 15 | 55 | 1,8-Octanedial |

*25% in $H_2O$

EXAMPLE 7

50% Ethanolic acrolein (30 µl) was added to a suspension of water-washed Albunex® microspheres (3 ml) in sterile water in a glass vial, and the vial was gently rolled on a standard roller mixer for 4 hours. Sodium cyanoborohydride (30 µl) from a stock solution prepared by dissolving 50 mg of reducing agent in 500 µl of water) was added in one batch to the bottom of the vial using a micropipette, and the vial was rolled overnight.

The resulting microsphere suspension was characterised by Coulter counter measurements; the relative gas volume of the microspheres was calculated and the suspension was standardised by adjusting its volume to a value where the gas volume was identical to that of a reference suspension of untreated Albunex® microspheres prior to echogenicity measurements being made.

EXAMPLES 8–12

The procedure of Example 7 was repeated except that acrolein was replaced by the aldehydes listed in the following Table:

| Example | Reagent µl | Reducing agent; µl | Gas Vol. % | Reagent (50% in ethanol) |
| --- | --- | --- | --- | --- |
| 7 | 30 | 30 | 100 | Acrolein |
| 8 | 30 | 30 | 98 | Crotonaldehyde |
| 9 | 30 | 30 | 44 | 2-Hexenal |
| 10 | 30 | 30 | 91 | Glutaraldehyde* |
| 11 | 15 | 15 | 61 | 2-Hydroxyadipaldehyde* |
| 12 | 15 | 15 | 59 | 1,8-Octanedial |

*25% in $H_2O$

EXAMPLE 13

An aqueous suspension of water-washed Albunex® microspheres (3 ml) was allowed to stand for 1 hour in a glass vial, whereafter 2.5 ml of the infranatant liquid below the floating microspheres were withdrawn using a pipette and 2.5 ml of pH 7 phosphate buffered saline were added. The vial was gently rolled on a standard roller mixer for 5 minutes to promote resuspension of the microspheres. 50% ethanolic acrolein (30 µl) was added to the bottom of the vial using a pipette and the vial was rolled for 4 hours. Sodium cyanoborohydride (30 µl from a stock solution prepared by dissolving 50 mg of reducing agent in 500 µl of water) was added and the vial was rolled overnight.

The resulting microsphere suspension was characterised by Coulter counter measurements; the relative gas volume of the microspheres was calculated and the suspension was standardised by adjusting its volume to a value where the gas volume was identical to that of a reference suspension of untreated Albunex® microspheres prior to echogenicity measurements being made.

EXAMPLES 14–21

The procedure of Example 13 was repeated except that acrolein was replaced by the aldehydes listed in the following Table:

| Example | Reagent µl | Reducing agent; µl | Gas Vol. % | Reagent (50% in ethanol) |
| --- | --- | --- | --- | --- |
| 13 | 30 | 30 | 71 | Acrolein |
| 14 | 30 | 30 | 66 | Methacrolein |
| 15 | 50 | 50 | 100 | Crotonaldehyde |
| 16 | 30 | 30 | 6 | 2-Pentenal |
| 17 | 30 | 30 | 5 | 2-Hexenal |
| 18 | 30 | 30 | 14 | 3-Dimethylaminoacrolein |

-continued

| Example | Reagent µl | Reducing agent; µl | Gas Vol. % | Reagent (50% in ethanol) |
|---|---|---|---|---|
| 19 | 30 | 30 | 71 | Glutaraldehyde* |
| 20 | 30 | 30 | 55 | 2-Hydroxyadipaldehyde* |
| 21 | 30 | 30 | 8 | 1,8-Octanedial |

*25% in $H_2O$

EXAMPLE 22

The procedure of Example 13 was repeated except that no sodium cyanoborohydride solution was added.

EXAMPLES 23-26

The procedure of Example 22 was repeated except that acrolein was replaced by the aldehydes listed in the following Table:

| Example | Reagent µl | Gas Vol. % | Reagent (50% in ethanol) |
|---|---|---|---|
| 22 | 30 | 80 | Acrolein |
| 23 | 30 | 83 | Crotonaldehyde |
| 24 | 30 | 67 | Glutaraldehyde* |
| 25 | 15 | 8 | 2-Hydroxyadipaldehyde* |
| 26 | 30 | 10 | 1,8-Octanedial |

*25% in $H_2O$.

The in vitro echogenicity and stability of the above standardised suspensions were determined by diluting each suspension with 7 ml of Isoton II (Coulter Electronics Limited, Luton, England) having a gas content similar to that of human venous blood. The acoustic transmission of each suspension was measured as a function of time, starting immediately after dilution and using a 3.5 MHz transducer.

After signal stabilisation all the products tested showed greater echogenicity than the reference suspension of untreated Albunex® microspheres.

A comparative experiment was performed repeating the procedure of Example 13 but using 33% aqueous formaldehyde in place of the ethanolic acrolein. The resulting product showed minimal in vitro echogenicity after signal stabilisation.

EXAMPLE 27

Albunex® microspheres were washed three times with pH 7 phosphate buffered saline and were resuspended in phosphate buffered saline (30 ml) in a glass vial. 25% aqueous glutaraldehyde (300 µl) was added and the vial was rolled for 20 hours at room temperature.

The crosslinked microspheres so obtained were subjected to size distribution modification by either (i) adding a saturated solution of air in phosphate buffered saline (prepared by standing phosphate buffered saline in a water bath at 37° overnight with gentle stirring to remove excess gas bubbles, and having a $pO_2$ of about 21 kPa) and incubating the vial on a roller for 3 hours at room temperature; (ii) adding a partially degassed solution of air in phosphate buffered saline (prepared by degassing the saturated solution from (i) for 1 hour at 37°, and having a $pO_2$ of about 10 kPa) and incubating the vial on a roller for 3 hours at room temperature; or (iii) placing the microsphere suspension in a pressure vessel, applying a pressure of air for 1 minute, resuspending the microspheres in phosphate buffered saline in a vial and rolling the vial for 5 minutes to give a homogeneous suspension.

The volumes of solution (relative to the volume of the microsphere suspension) and air pressures employed and the gas volume concentrations of the microspheres are detailed in the following Table:

| Method | Volume/ Pressure | Microsphere volume concentration (%) | Microsphere volume concentration corrected for dilution (%) |
|---|---|---|---|
| — | — | 1.76 | 1.76 |
| (i) | 2 vols | 0.84 | 1.68 |
| (i) | 5 vols | 0.17 | 0.85 |
| (i) | 9 vols | 0.08 | 0.72 |
| (ii) | 1.5 vols | 0.85 | 1.28 |
| (ii) | 2 vols | 0.42 | 0.84 |
| (ii) | 3 vols | 0.14 | 0.42 |
| (iii) | 26 kPa | 1.30 | 1.30 |
| (iii) | 66 kPa | 0.73 | 0.73 |

Echogenicity measurements were made on microsphere suspensions standardised to contain uniform gas volumes. The optimum degree of size distribution modification, i.e. that which gave stable acoustic attenuation at as high a level as possible, was found to be about 50% reduction of the microsphere volume, e.g. as obtained by addition of about 5 volumes of saturated phosphate buffered saline or 2 volumes of partially degassed phosphate buffered saline or by application of an overpressure of 66 kPa of air. Addition of higher volumes of phosphate buffered saline or application of higher pressures yielded microspheres which exhibited high stability but reduced acoustic attenuation, the use of extreme volumes/pressures leading to collapse of the microspheres and consequent loss of acoustic attenuation.

EXAMPLE 28

Size distribution modified microspheres were prepared in accordance with method (iii) of Example 27, applying an air pressure of 66 kPa. The resulting microspheres were washed three times with phosphate buffered saline and concentrated by flotation/removal of the underlying solution. Physical characteristics of the microspheres (a) before size distribution modification, (b) after size distribution modification, (c) after washing and (d) after concentration are shown in the following Tables:

| Stage | Microsphere concentration ($10^8$/ml) | Mean diameter (µm) | Microsphere volume concentration (%) |
|---|---|---|---|
| (a) | 8.59 | 2.99 | 2.75 |
| (b) | 8.75 | 2.41 | 0.96 |
| (c) | 3.01 | 2.50 | 0.35 |
| (d) | 23.6 | 2.64 | 3.16 |

| Stage | Initial acoustic attenuation (dB/cm) | Acoustic attenuation after 90 seconds (dB/cm) |
|---|---|---|
| (a) | 15.5 | 8.4 |
| (b) | 11.5 | 11.7 |
| (c) | 9.5 | 10.1 |
| (d)[1] | 15.1 | 15.7 |
| (d)[2] | 10.0 | 10.4 |

[1]using 0.5 µl gas volume
[2]using 0.3 µl gas volume

| | Size distribution | |
|---|---|---|
| Stage | 0–4 μm (%) | 4–10 μm (%) |
| (a) | 79 | 21 |
| (b) | 95 | 5 |
| (c) | 94 | 6 |
| (d) | 92 | 8 |

EXAMPLE 29

Albunex® microspheres were washed three times with pH 7 phosphate buffered saline and were resuspended in phosphate buffered saline (30 ml) in a glass vial. 50% ethanolic crotonaldehyde (300 μl) was added and the vial was rolled for 20 hours at room temperature. Sodium cyanoborohydride (300 μl from a stock solution prepared by dissolving 100 mg of the reducing agent in 1 ml of water) was then added and the vial was rolled for a further hour at room temperature.

The crosslinked microspheres so obtained were subjected to size distribution modification using the methods described in Example 27 and were found to give similar results to size distribution modified glutaraldehyde-crosslinked microspheres.

EXAMPLE 30

Isoton II (250 ml) in a capped 500 ml flask was placed in a water bath at 37° and saturated with air overnight, with magnetic stirring. The flask was thereafter placed on a magnetic stirrer at ambient temperature and stirred at 250–300 rpm. Within 5 minutes of removing the flask from the water bath, a suspension of glutaraldehyde-crosslinked albumin microspheres prepared as described in Example 24 using 300 μl of reagent and having a gas volume of 25% (30 ml) was injected by means of a syringe and needle through the cap into the Isoton, and stirring was continued for 4 hours. The flask was then left standing overnight to permit flotation of the microspheres. The Isoton was removed from the bottom of the flask using a syringe and needle, a further needle being placed in the cap to permit aspiration, whereafter phosphate buffered saline (15 ml) was added and the flask was rolled for 20 minutes to promote homogeneous suspension of the microspheres. The resulting suspension was characterised by Coulter counter analysis and echogenicity measurement, as shown in the following Table:

| | 0–4 μm (%) | 4–10 μm (%) | >10 μm (%) | Initial Acoustic attenuation (dB/cm) | Acoustic attenuation after 90 seconds (dB/cm) |
|---|---|---|---|---|---|
| Before size distribution modification | 73 | 26.5 | 0.5 | 5.6 | 2.4 |
| After size distribution modification | 89 | 11 | 0 | 8.9 | 8.9 |

EXAMPLE 31

The procedure of Example 30 was repeated using 50% ethanolic acrolein (300 μl) as the crosslinking agent to give microspheres having a gas volume prior to size distribution modification of 12%.

We claim:

1. Contrast agents comprising microbubbles of gas or a gas precursor encapsulated in a shell of protein crosslinked by reaction in an aqueous medium at substantially neutral pH with a bifunctional aldehyde capable of effecting crosslinking of the protein, characterised in that the crosslinked protein shell has additionally been stabilized by reaction with a reducing agent serving to reduce the double bond of a Schiff's base.

2. Contrast agents as claimed in claim 1 wherein the protein is albumin, gelatin or γ-globulin.

3. Contrast agents as claimed in claim 2 wherein the protein is human serum albumin.

4. Contrast agents as claimed in claim 1 wherein the aldehyde is a dialdehyde or an α,β-unsaturated aldehyde.

5. Contrast agents as claimed in claim 4 wherein the aldehyde is selected from glutaraldehyde, adipaldehyde, 2-hydroxyadipaldehyde, 1,8-octanedial, acrolein, 3-dimethylaminoacrolein, methacrolein, crotonaldehyde, 2-pentenal and 2-hexenal.

6. Contrast agents as claimed in claim 1 comprising gas microbubbles which have been subjected to size distribution modification.

7. Contrast agents as claimed in claim 6 characterised in that they show no loss of contrast effect over 90 seconds during in vitro monitoring of such contrast effect.

8. Contrast agents as claimed in claim 1 characterised in that at least 85% of the microbubbles have sizes up to 4 μm and the remainder have sizes in the range 4–10 μm.

9. Contrast agents as claimed in claim 8 wherein at least 90% of the microbubbles have sizes up to 4 μm.

10. A method of generating enhanced images of a human or non-human animal body which comprises administering to said body a contrast agent as claimed in claim 1 and generating an ultrasound or MR image of at least a part of said body.

11. A process for the preparation of a microbubble contrast agent as claimed in claim 1 wherein a protein is crosslinked by reaction in an aqueous medium at substantially neutral pH with a bifunctional aldehyde capable of effecting crosslinking of the protein, a gas or a gas precursor being encapsulated in said protein before, during or after said crosslinking reaction, and wherein the crosslinked protein is also reacted with a reducing agent serving to reduce the double bond of a Schiff's base, or wherein such a reducing agent is present during the crosslinking reaction.

12. A process as claimed in claim 11 which comprises crosslinking preformed sonicated protein-based microspheres.

13. A process as claimed in claim 11 wherein the crosslinking is effected at a pH in the range 6–8.

14. A process as claimed in claim 13 wherein the crosslinking is effected at a pH of about 7.

15. A process as claimed in claim 11 wherein the crosslinking is effected in an aqueous buffer system.

16. A process as claimed in claim 15 wherein the buffer is phosphate buffered saline.

17. A process as claimed in claim 11 wherein the reducing agent is sodium borohydride or sodium cyanoborohydride.

18. A process as claimed in claim 11 for the preparation of a gas-containing contrast agent wherein the microbubbles are also subjected to size distribution modification.

19. A process as claimed in claim 18 wherein size distribution modification is effected after crosslinking of the protein.

20. A process as claimed in claim 18 wherein size distribution modification is effected by application of an external pressure of gas to the microbubbles or a suspension thereof.

21. A process as claimed in claim 18 wherein size distribution modification is effected by treating the microbubbles with a liquid in which the gas content thereof is soluble.

22. A process as claimed in claim 18 wherein the mean volume of the microbubbles is reduced by 40–60%.

23. Contrast agents as claimed in claim 1 wherein the microbubbles comprise gas selected from the group consisting of air, nitrogen, oxygen, hydrogen, nitrous oxide, carbon dioxide, helium, argon, sulphur hexafluoride, low molecular weight hydrocarbons and fluorinated low molecular weight hydrocarbons.

* * * * *